US006414029B1

(12) United States Patent
Shechter et al.

(10) Patent No.: US 6,414,029 B1
(45) Date of Patent: Jul. 2, 2002

(54) VANADIUM COMPLEXES OF MONOHYDROXAMATES AND PHARMACEUTICAL COMPOSITIONS COMPRISING THEM

(75) Inventors: Yoram Shechter; Matityahu Fridkin, both of Rehovot; Itzhak Goldwasher, Rishon-le-Zion; Eytan Gershonov, Hod Hasharon, all of (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/508,411

(22) PCT Filed: Sep. 10, 1998

(86) PCT No.: PCT/IL98/00441

§ 371 (c)(1),
(2), (4) Date: May 18, 2000

(87) PCT Pub. No.: WO99/12875

PCT Pub. Date: Mar. 18, 1999

(30) Foreign Application Priority Data

Sep. 11, 1997 (IL) .................................................. 121748

(51) Int. Cl.$^7$ .................. A61K 31/16; A61K 31/28; C07C 259/04; C07C 9/00
(52) U.S. Cl. .................. 514/578; 562/621; 562/623; 562/573
(58) Field of Search .................. 562/621, 623, 562/573; 514/578

(56) References Cited

U.S. PATENT DOCUMENTS 5,338,759 A    8/1994    Schecter et al.

FOREIGN PATENT DOCUMENTS

EP    0 305 264    3/1989
EP    0 737 671    10/1996

OTHER PUBLICATIONS

Brichard, S.M et al., "The role of vanadium in the mangement of diabetes," Trends in Pharmacological Sciences, 1995, 16(8), 265–270.

Brown, D.A. et al., "Conformation behaviour of hydroxamic acids: ab initio and structural studies," J. Chem. Soc., 1996, 2, 2673–2679.

Cohen, N. et al., "Oral Vanadyl Sulfate Improves Hepatic and Peripheral Insulin Sensitivity in Patients with Non–Insulin–dependent Diabetes Mellitus," J. Clin. Invest. 1995, 95, 2051–2509.

Li, J. et al., "Evidence for the Distinct Vanadyl(+4)–Dependent Activating System for Manifesting Insulin–like Effects," Biochemistry, 1996, 35, 8314–8318.

Shechter, Y. et al., "Hydrophobic Carriers of Vanadyl Ions Augment the Insulinomimetic Actions of Vanadyl Ions in Rat Adipocytes," Biochemistry 31, 1992, 2063–68.

Shechter, Y. et al, "Insulin–Like Actions of Vanadate are mediated in an insulin–receptor–independent manner via non–receptor protein tyrosine kinases and protein phosphotyrosine phosphates," Molec. Cell Biochem., 1995, 153, 39–47.

Tournaire, R. et al., "Therapeutic Effects of D–Aspartic Acid β–Hydroxymate (DAH) on Friend Erythroleukemia," Int. J. Cancer, 1994, 58, 420–425.

Vila, J. et al., "In Vitro and in vivo anti–tumor activity of L–Glutamic Acid Monohydroxamate against L1210 Leukemia and B16 Melanoma," Int. J. Cancer, 1990, 45, 737–743.

Goldine, A. et al., "In vivo and in vitro studies of vanadate in human and rodent diabetes mellitus," Mol. and Cellular Biochemistry, 1995, 153, 217–231.

Fantus, I.G. et al, "Multifunctional actions of vanadium compounds on insulin signaling pathways: Evidence for preferential enhancement of metabolic versus mitogenic effects," Mol. and Cellular Biochemistry, 1998, 182: 109–119.

*Primary Examiner*—Charanjit S. Aulakh
(74) *Attorney, Agent, or Firm*—Browdy and Neimark (57) ABSTRACT

Monohydroxamate vanadium complexes of the formula (1): R—CO—NHOH.X, wherein R is a residue selected from: (i) $H_2N$—CH(COY)—$(CH_2)_n$—, wherein n is 1, 2 or 3, and Y is OH or $NH_2$; (ii) $H_2N$—$CH_2$—S—$CH_2$—; and (iii) pyridyl, piperidyl or tetrahydroisoquinolinyl; and X is a vanadium compound selected from a vanadyl ($VO^{2+}$), metavanadate ($VO_3-$) or vanadate ($VO_4^{3-}$) salt, are useful for inducing normoglycemia and/or reducing blood glucose levels in diabetic patients.

18 Claims, 9 Drawing Sheets

VANADIUM COMPLEXES OF MONOHYDROXAMATES AND PHARMACEUTICAL COMPOSITIONS COMPRISING THEM

CROSS REFERENCE TO RELATED APPLICATION

The present application is the national stage under 35 U.S.C. 371 of PCT/IL98/00441, filed Sep. 10, 1998.

FIELD OF INVENTION

The present invention relates to vanadium complexes of monohydroxamates and to pharmaceutical compositions comprising them useful for the treatment of diabetes.

ABBREVIATIONS Asp(β)HXM, L-aspartic acid β-monohydroxamate; CytPTK, cytosolic protein-tyrosine kinase; Glu(γ)HXM, L-glutamic acid γ-monohydroxamate; HXM, monohydroxamate; InsRTK, insulin receptor tyrosine kinase; IRS-1, Insulin receptor substrate 1; PTK, protein tyrosine kinase; KRB, Krebs Ringer bicarbonate; NaVO$_3$, sodium metavanadate; STZ, streptozocin; VOSO$_4$, vanadyl sulphate; VOCl$_2$, vanadyl chloride.

BACKGROUND OF THE INVENTION

Intensive studies have been carried out in the last two decades on the insulinomimetic effects of vanadium (reviewed in Shechter et al.,1995). In vitro, vanadium salts mimic most of the effects of insulin on the main target tissues of the hormone, and in vivo they induce normoglycemia, and improve glucose homeostasis in insulin-deficient and insulin-resistant diabetic rodents (reviewed in Brichard and Henquin, 1995). In the basic research frontier, data continues to accumulate showing that vanadium salts manifest their insulin-like metabolic effects through alternative pathways, not involving insulin-receptor tyrosine kinase activation, nor phosphorylation of insulin-receptor substrate 1 (IRS-1). The key players of his back-up system appear to involve inhibition of protein-phosphotyrosine phosphatases and activation of nonreceptor protein tyrosine kinases (reviewed in Brichard and Henquin, 1995).

Vanadium is an ultra trace element in mammals. The dietary intake varies between 10–60 μg day$^{-1}$, and the intracellular concentration is approximately 20 nM (reviewed in Shechter et al., 1995 and Brichard and Henquin, 1995). The bulk of the intracellular vanadium is probably in the vanadyl (+4) form. Acute oral administration of vanadium compounds proved to be moderately toxic. Nevertheless, the profound anti-diabetic effects of oral vanadium therapy in insulin-deficient and insulin-resistant diabetic rodents (reviewed in Brichard and Henquin, 1995) encouraged the start of clinical studies. Small doses of vanadium (100–125 mg/person/day, over a period of 3 weeks) were allowed and, although 100 fold lower than those used in most animal studies, several beneficial effects were observed (Cohen et al., 1995).

Organically chelated vanadium (+4) complexes are about 5 fold more potent than free vanadium (+4) in facilitating the metabolic effects of insulin in vitro (Li et al., 1996) and in STZ-rats in vivo (Sakurai et al., 1995). The theoretical basis for that is still under study, and is likely the result of stabilizing the more potent insulin-like vanadium species.

Vanadium salts mimic the metabolic effects of insulin through alternative insulin-independent machinery components in vitro and can overcome states of insulin-resistance in diabetic rodents in vivo. As such vanadium therapy could make a useful, attractive and complementary approach to insulin therapy, provided that vanadium salts were less toxic or certain manipulation could be made to carry on vanadium therapy with no, or reduced quantities of, exogenous vanadium source.

Israel Patent No. 99666 and corresponding U.S. Pat. No. 5,338,759 of the same applicants describe vanadyl complexes of dihydroxamates of the formula:

which are said to be useful for the treatment of diabetes, but were later found by the inventors to be unsuitable in vivo for normalizing blood glucose levels in model diabetic rats.

Hydroxamic acid derivatives were shown to be involved in the microbial transport of iron, and therefore suggested for treatment of conditions of iron deficiency. They are also inhibitors of urease activity and indicated for the treatment of hepatic coma. Much of their biological activities are related to their potency to chelate a variety of metals. In the majority of metal chelates formed by hydroxamic acids, coordination occurs by deprotonation of the OH group and subsequent (O,O) coordination with the carbonyl oxygen and deprotonated OH.

Amino acid monohydroxamates are simple, nontoxic derivatives of amino acids. D-Aspartic acid β-hydroxamate (D-Asp(β)HXM) was shown to have antitumoral activity on murine leukemia L5178Y, both in vitro and in vivo, and is active against Friend leukemia cells in vitro (Tournaire et al., 1994). L-Glutamic acid (γ)-monohydroxamate (Glu(γ)HXM) is cytotoxic against leukemia L1210 cells in vitro, and against leukemia L1210 and melanoma B16 cells in vivo (Vila et al., 1990).

SUMMARY OF THE INVENTION

It has now been found in accordance with the present invention that certain amino acid monohydroxamates (HXM), in particular the L-forms of glutamic acid γ-monohydroxamate (Glu(γ)HXM) and aspartic acid β-monohydroxamate (Asp(β)HXM), interact with vanadium (+4) and vanadium (+5). At a 1:1 or 2:1 HXM: vanadium molar stoichiometry, they largely potentiate the insulinomimetic potencies of vanadium (+4) and (+5) in vitro, and normalize the blood glucose level of streptozocin-treated rats in vivo.

The present invention relates to novel vanadium complexes of monohydroxamates of the formula (I):

wherein
R is a residue selected from:
   (i) H$_2$N—CH (COY)—(CH$_2$)$_n$—
   (ii) H$_2$N—CH (COOH)—CH$_2$—S—CH$_2$—; and
   (iii) pyridyl, piperidyl or tetrahydroisoquinolinyl;
wherein n is 1, 2 or 3, and Y is OH or NH$_2$; and X is a vanadium compound selected from a vanadyl (VO$^{2+}$), metavanadate (VO$_3^-$) or vanadate (VO$_4^{3-}$) salt.

According to the present invention, in the monohydroxamates of (i) above, n is preferably 1 or 2, namely the β- and γ-monohydroxamates of L-aspartic acid and L-glutanic acid, respectively. In a most preferred embodiment, the amino acid monohydroxamate is Glu(γ)HXM, that was found to be more effective in the manifestation of the metabolic effects of insulin in rat adipocytes as compared to various α-amino acid monohydroxamates.

Interestingly enough, among all known vanadium chelators disclosed in the literature such as acetylacetonate, bispicolinato and the dihydroxamate RL-252 described in the above-mentioned U.S. Pat. No. 5,338,759, amino acid monohydroxamates are unique in their capacity to produce insulin effects, in vitro, in the absence of externally added vanadium, indicating that amino acid monohydroxamates might be capable of converting the minute quantity of intracellularly located vanadium (+4, ~20 nM) into an insulinomimetically-active species. Further studies in vitro revealed that Glu(γ)HXM facilitates all the physiologically relevant bioeffects of insulin. These include activation of hexose uptake and inhibition of isoproterenol mediated lipolysis. Quite importantly, activation by Glu(γ)HXM is additive to maximal effect produced by a saturated concentration of insulin.

Among the monohydroxamates of (iii) above, preferred are the 3-pyridyl radical, namely the nicotinic acid hydroxamate, the 2- or 3-piperidyl radical and the 3-tetrahydroisoquinolinyl radical.

The monohydroxamates used in the present invention are soluble in water in contrast to the dihydroxamates of the above mentioned U.S. Pat. No. 5,338,759, that are water insoluble. Thus the vanadium complexes of the present invention can be prepared by simple dissolution in water of the monohydroxamate and of the vanadium salt.

Examples of vanadium salts used to form the complexes used in the compositions of the present invention are, without being limited to, $VOCl_2$ (+4), $VOSO_4$ (+4), $NaVO_3$ (+5) and $Na_3VO_4$ (+5).

Various HXM: vanadium salt stoichiometric molar ratios of the complexes are envisaged by the present invention, but 1:1 and 2 HXM: 1 vanadium salt molar ratios are preferred.

The complexes of formula I of the invention are prepared by mixing water solutions of the monohydroxamate and the vanadium salt, freezing and lyophilizing the solution, thus obtaining a dry powder that can be stored, for example, at room temperature.

The invention further provides a pharmaceutical composition useful for the treatment of diabetes, particularly for reduction of blood glucose levels and induction of normoglycemia in diabetic patients, comprising a vanadium complex of a monohydroxamate of formula (I) as an active ingredient and, optionally, a pharmaceutically acceptable carrier. Said compositions may be used for treatment of both insulin-dependent diabetes mellitus (IDDM) and non-insulin-dependent diabetes mellitus NIDDM).

The dosage to be administered will depend on the conditions of the diabetic patient and may be within a range of from 0.2 mg/kg to 2 mg/kg daily. Since the allowed amount of vanadium being used in diabetic patients in clinical trials today is about 2 mg/kg/day, the minimum amount provided by the present invention represents a 10 fold increase in efficacy.

The compositions of the invention comprising the vanadium complex of formula I may be presented in soluble form, such as drops, or in the form of capsules or tablets and are preferably administered orally. They may be administered alone or in combination with insulin.

The vanadium complex of formula I may also be generated in vivo by separate administration of the vanadium salt and of the monohydroxamate. The invention thus further comprises a pharmaceutical package comprising a pharmaceutical composition comprising a monohydroxamate of the formula R—CO—NHOH, wherein R is a residue selected from: (i) $H_2N$—CH (COY)—$(CH_2)_n$—; (ii) $H_2N$—CH (COOH)—$CH_2$—S—$CH_2$—; and (iii) pyridyl, piperidy or tetrahydroisoquinolinyl; and n is 1, 2 or 3, and Y is OH or $NH_2$; and a pharmaceutical composition comprising a vanadium compound selected from a vanadyl ($VO^{2+}$), metavanadate ($VO_3^-$) or vanadate ($VO_4^{3-}$) salt, with instructions how to administer them. Preferably, the composition comprising the vanadium salt is administered prior to the monohydroxamate composition. The two ingredients may also be comprised within a compartment of a single composition, e.g. a capsule, separated by a non-permeable membrane.

Since a monohydroxamate of formula R—CO—NHOH above, particularly Glu(γ)HXM, can by itself associate to endogenous intracellular vanadium, modifying the latter into an active species that evoke the metabolic responses of insulin, the invention further envisages a pharmaceutical composition for the treatment of diabetes comprising a monohydroxamate of the formula R—CO—NHOH, wherein R is a residue selected from: (i) $H_2N$—CH (COY)—$(CH_2)_n$—; (ii) $H_2N$—CH (COOH)—$CH_2$—S—$CH_2$—; and (iii) pyridyl, piperidyl or tetrahydroisoquinolinyl; and n is 1, 2 or 3, and Y is OH or $NH_2$.

The invention further relates to the use of a monohydroxamate of the formula R—CO—NHOH, wherein R is a residue selected from: (i) $H_2N$—CH (COY)—$(CH_2)_n$—; (ii) $H_2N$—CH (COOH)—$CH_2$—S—$CH_2$—; and (iii) pyridyl, piperidyl or tetrahydro-isoquinolinyl; and n is 1, 2 or 3, and Y is OH or $NH_2$, for the preparation of a pharmaceutical composition for the treatment of diabetes.

In another embodiment, the invention relates to a method for reduction of blood glucose levels in a diabetic patient which comprises administering to said patient an effective amount of a vanadium complex of a monohydroxamate of formula (I) herein, or of effective amounts of a monohydroxamate of the formula R—CO—NHOH herein and a vanadium compound selected from a vanadyl ($VO^{2+}$), metavanadate ($VO_3^-$) or vanadate ($VO_4^{3-}$) salt, or of effective amounts of a monohydroxamate of the formula R—CO—NHOH herein, alone or in combination with insulin therapy.

In a further embodiment, the invention relates to a method for inducing normoglycemia in a diabetic patient which comprises administering to said patient an effective amount of a vanadium complex of a monohydroxamate of formula (I) herein, or of effective amounts of a monohydroxamate of the formula R—CO—NHOH herein and a vanadium compound selected from a vanadyl ($VO^{2+}$), metavanadate ($VO_3^-$) or vanadate ($VO_4^{3-}$) salt, or of effective amounts of a monohydroxamate of the formula R—CO—NHOH herein, alone or in combination with insulin therapy.

DESCRIPTION OF THE PREFERRED EMBODIMENTS

According to the present invention, a unique and specific potentiation of vanadium insulinomimetic potency is achieved by certain monohydroxamate complexants of vanadium. Particularly, L-glutamic acid (γ) monohydroxamate (Glu(γ)HXM) potentiates ≈7–10 fold vanadium (+5) in activating glucose metabolism in rat adipocytes, and elevates 5–7-fold the efficacy of vanadate to lower blood glucose levels in STZ-treated diabetic rats in vivo Potentiation is maximal at a 2:1 molar ratio of L-Glu(γ) HXM:Vanadium. Both nonmodified α-amino and α-carboxyl moieties of L-Glu(γ)HXM are essential for the potentiation. Moreover, the synergistic action of L-Glu(γ) HXM is stereospecific and is not facilitated with D-Glu(γ) HXM, although the latter also complexes with vanadium. Interestingly enough, of all documented vanadium complexants that potentiate the insulinomimetic actions of vanadium, L-Glu(γ)HXM is unique in the sense of activating lipogenesis in rat adipocytes in the absence of exogenously added vanadium as well. It is herein further established that this effect manifests through the vanadium pathway by experimental data indicating that L-Glu(γ)HXM is capable of converting the minute physiological quantity of endogenously present vanadium in rat adipocytes into an insulinomimetic active species. Chemophysical studies of this active complex, indicates a unique physicochemical features. Vanadium is maintained at the +5 oxidation state, at physiological pH value, at equilibrium also if prepared with the vanadyl +4 cation.

The in vitro screening assay used in the present invention indicates that, in addition to Glu(γ)HXM, also L-Asp(β) HXM and nicotinicacid-HXM (at 1:1 molar ratio) potentiate the insulinomimetic potency of vanadium(+4) as well. Their synergizing effect is ~85% and ~57% of that exerted by Glu(γ)HXM. In contrast, (α-amino acid hydroxamates as well as the D-isomers of both Glu(γ)HXM and Asp(β)HXM, did not potentiate the insulinomimetic eficacy of VOCl$_2$.

The invention will now be illustrated by the following non-limiting examples.

Experimental Procedures (a) Materials. D-[U-$^{14}$C] glucose and 2deoxy-D-[G-$^3$H] glucose were purchased from New England Nuclear (Boston, Mass.). Collagenase type I (134 U/mg) was obtained from Worthington Biochemicals (Freehold, N.J.). Porcine insulin was purchased from Eli Lilly Co. (Indianapolis, Ind.). Phloretin, 2 deoxyglucose, L-glutamic acid γ-monohydroxamate (Glu(γ)HXM), glycine hydroxamate (Gly-HXM), L-isoleucine hydroxamate (isoleu-HXM), L-tryptophan hydroxamate (Trp-HXM), L-tyrosine hydroxamate (Tyr-HXM) and L-cystine dihydroxamate (Cystine (HXM$_2$)) were purchased from Sigma Chemical Co., St. Louis, Mo.

Krebs-Ringer bicarbonate (KRB) buffer, (pH 7.4), contained 110 mM NaCl, 25 mM NaHCO$_3$, 5 mM KCl, 1.2 mM KH$_2$PO$_4$, 1.3 mM CaCl$_2$, 1.3 mM MgSO$_4$.

All other chemicals and reagents used in His study were of analytical grade.

(b) Streptozocin(STZ)-treated rats: Diabetes was induced by a single intravenous injection of a freshly prepared solution of streptozocin (55 mg/kg of body weight) in 0.1 M citrate buffer (pH 4.5). The effect of the tested compounds on blood glucose level was determined 14 days following induction of diabetes.

(c) Cell preparation and Lipogenesis bioassay: Rat adipocytes were prepared essentially by the method of Rodbell, 1964. The fat pads of male Wistar rats were cut into small pieces with scissors and suspended in 3 ml of KRB buffer. The digestion was performed with collagenase (type 1, 134 units/mg; 1 mg/ml) in a 25-ml flexible plastic bottle under an atmosphere of carbogen (95% O$_2$, 5% CO$_2$) for 40 min at 37° C. with vigorous shaking. Cell preparations showed more than 95% viability by Trypan blue exclusion, at least 3 hours after digestion. Five ml of buffer was then added, and the cells were passed through a mesh screen. The cells were then allowed to stand for several minutes in a 15-ml plastic test tube at room temperature, floating, and the buffer underneath was removed. This procedure (suspension, floating, and removal of buffer underneath) was repeated three times.

In the lipogenic assay, for measurement of glucose uptake and its incorporation into lipids (lipogenesis), the adipocyte suspensions (3×10$^5$ cells/ml) were divided into plastic vials (0.5 ml per vial) and incubated for 60 min at 37° C. under an atmosphere of carbogen with 0.2 mM [U-$^{14}$C]glucose (4–7 mCi/mol), in either the absence or presence of insulin (100 ng/ml), and the complexes to be tested. Lipogenesis was terminated by adding toluene-based scintillation fluid (1.0 ml per vial) and the radioactivity in extracted lipids was counted (Moody et al., 1974). In a typical experiment insulin-stimulated lipogenesis was 4–5 fold higher than basal. Vbasal ≈2000 cpm per 3×10$^5$ cell/h; Vinsulin ≈8,000–10,000 cpm per 3×10$^5$ cell/h.

EXAMPLES

Example 1

In Vitro Potentiation of the Lipogenic Capacity of Low Concentrations of VOCl$_2$ (10 mM) by Equimolar Concentrations of Monohydroxamates The following protocol was found to be a reliable assay in vitro, that is indicative for the potentiation effects of the amino acid monohydroxamates on vanadium (+4) in STZ-rats in vivo.

Activation of lipogenesis was performed as described in Experimental Procedures, section (c), using 10 μM solutions of various free amino acid monohydroxamates (HXM), 10 μM solution of VOCl$_2$ ($_{+}$4 ), or 10 μM solution of freshly prepared 1:1 complex of amino acid-HXM:VOCl$_2$.

The following amino acid monohydroxamates were tested: L-glutamic acid γ-monohydroxamate [Glu(γ)HXM], glycine hydroxamate (Gly-HXM), L-isoleucine hydroxamate (Ile-HXM), L-tryptophan hydroxamate (Trp-HXM), L-tyrosine hydroxamate (Tyr-HXM), L-cystine dihydroxamate [Cys(HXM)$_2$], L-lysine hydroxamate (Lys-HXM), nicotinic acid hydroxamate (Nic-HXM), L-arginine hydroxamate (Arg-HXM), L-histidine hydroxamate (His-HXM), D-glutamic acid γ-monohydroxamate [D-Glu(γ)HXM], N-acetyl-L-glutamic acid γ-monohydroxamate [N-acetyl-Glu(γ)HXM], L-aspartic acid β-monohydroxamate [Asp(β) HXM], aminoisobutyric acid monohydroxamate [Aib-HXM].

The results are summarized in Tables I and II. As shown in Table 1, Glu(γ)HXM (10 μM), VOCl$_2$ (10 mm) or their 1:1 complex produced 22%, 40% and 117%, respectively, of maximal insulin response. The net potentiating effect amounted therefore to 51%. Nic-HXM also potentiates the lipogenic capacity of VOCl$_2$ (29%, net potentiating effect Table I). Other amino acid hydroxamates studied did not potentiate the effect of vanadium (+4). The same is valid for D-Glu(γ)HXM and for N-acetyl-Glu(γ)HXM, indicating that for Glu(γ)HXM, the free α-amino group and the L-isomeric form are essential for the potentiation.

TABLE I

Potentiation of the lipogenic capacity of low concentrations of VOCl$_2$ (10 μM) by equimolar concentrations of amino acid monohydroxamates

| | Percent of maximal effect of insulin | | | |
|---|---|---|---|---|
| | Amino acid —HXM only (10 μM) | VOCl$_2$ Only (10 μM) | VOCl$_2$:HXM 1:1 (10 μM) | Net Potentiating Effect (%) |
| Glu(γ)HXM | 22% | 40% | 117% | 51% |
| Nic-HXM | 11% | 40% | 80% | 29% |
| Aib-HXM | 0% (−3%) | 40% | 22% | 0 |
| Lys-HXM | 0% (−4%) | 40% | 36% | 0 |
| D-Glu(γ)HXM | 1% | 40% | 17% | 0 |
| N-acetyl Glu(γ)HXM | 0% | 40% | 24% | 0 |
| L-Asp(β)HXM | 8% | 11% | 73% | 54% |
| Arg-HXM | 4% | 11% | 17% | ~2% |
| Trp-HXM | 2% | 11% | 22% | ~9% |
| His-HXM | 4% | 11% | 18% | ~3% |

TABLE II

Insulinomimetic effect of various VOCl$_2$:HXM (1:1), in comparison to L-Glu(γ)HXM:VOCl$_2$(1:1)

| 1:1 complex of VOCl$_2$ and: | % activity relative to Glu(γ)HXM VOCl$_2$ |
|---|---|
| L-Glu(γ)HXM | 100% |
| L-Asp(β)HXM, Nic-HMX | 70% |
| D-Glu(γ)HXM, N-acetyl Glu(γ)HXM, D-Aspβ)HXM Aib-HXM, Lys-HXM, Arg-HXM, Trp-HXM, His-HXM | 0% |

Example 2

Figure 1:
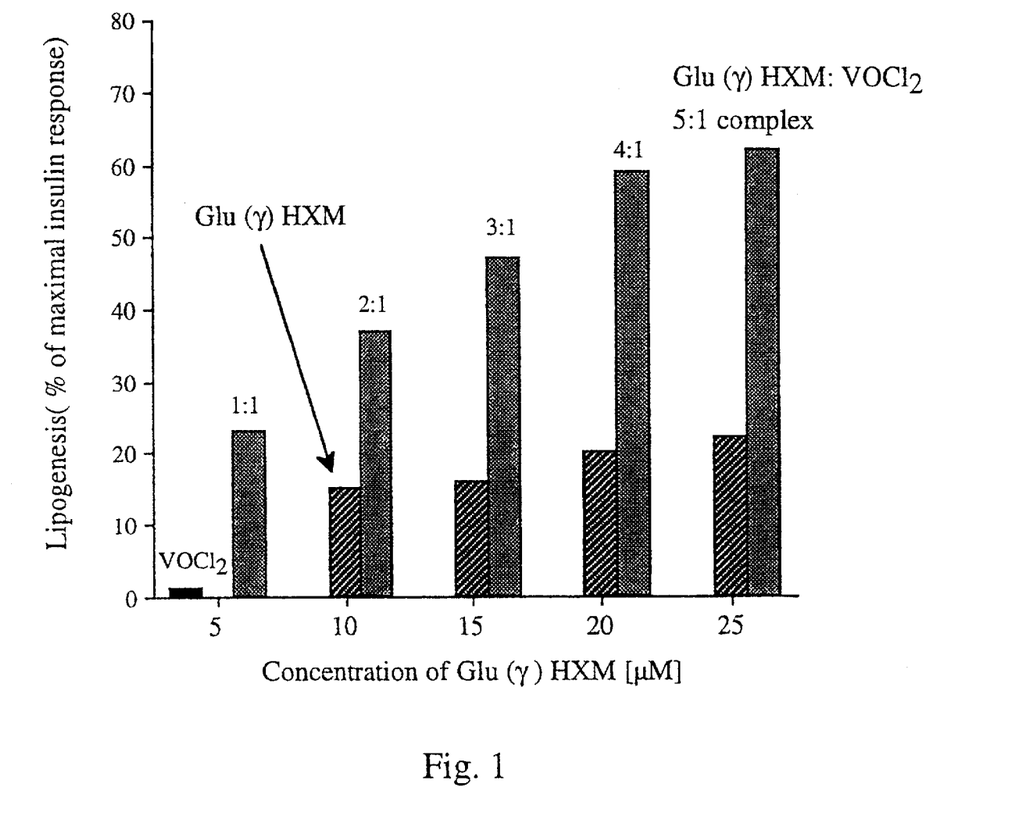
FIG. 1 shows concentration-dependent activation of lipogenesis by 1:1 to 1:5 complexes of Glu(γ)HXM: $VOCl_2$ (+4) in comparison to free $VOCl_2$ and free Glu (γ)HXM.

Concentration-dependent in Vitro Activation of Lipogenesis by a 1:1 to 1:5 Complex of Glu(γ) HXM:VOCl$_2$ in Comparison to Free VOCl$_2$ and Free Glu(γ)HXM In order to determine the most effective ratio of the Glu(γ)HXM:VOCl$_2$ complex to synergize the insulinomimetic potency of vanadium, lipogenesis was performed as described in Experimental Procedures, section (c), using 1:1 to 5:1 complexes of Glu(γ)HXM:VOCl$_2$, free VOCl$_2$, and free Glu(γ)HXM. The results shown in FIG. 1 demonstrate that, in comparison to the lipogenic potency of 5 mM VOCl$_2$ alone and complexed with increasing concentrations of Glu(γ)HXM (5–25 μM), a 1:1 stoichiometric complex of both was found most effective in synergizing the insulinomimetic potency of vanadium (+4).

Example 3

Figure 2:
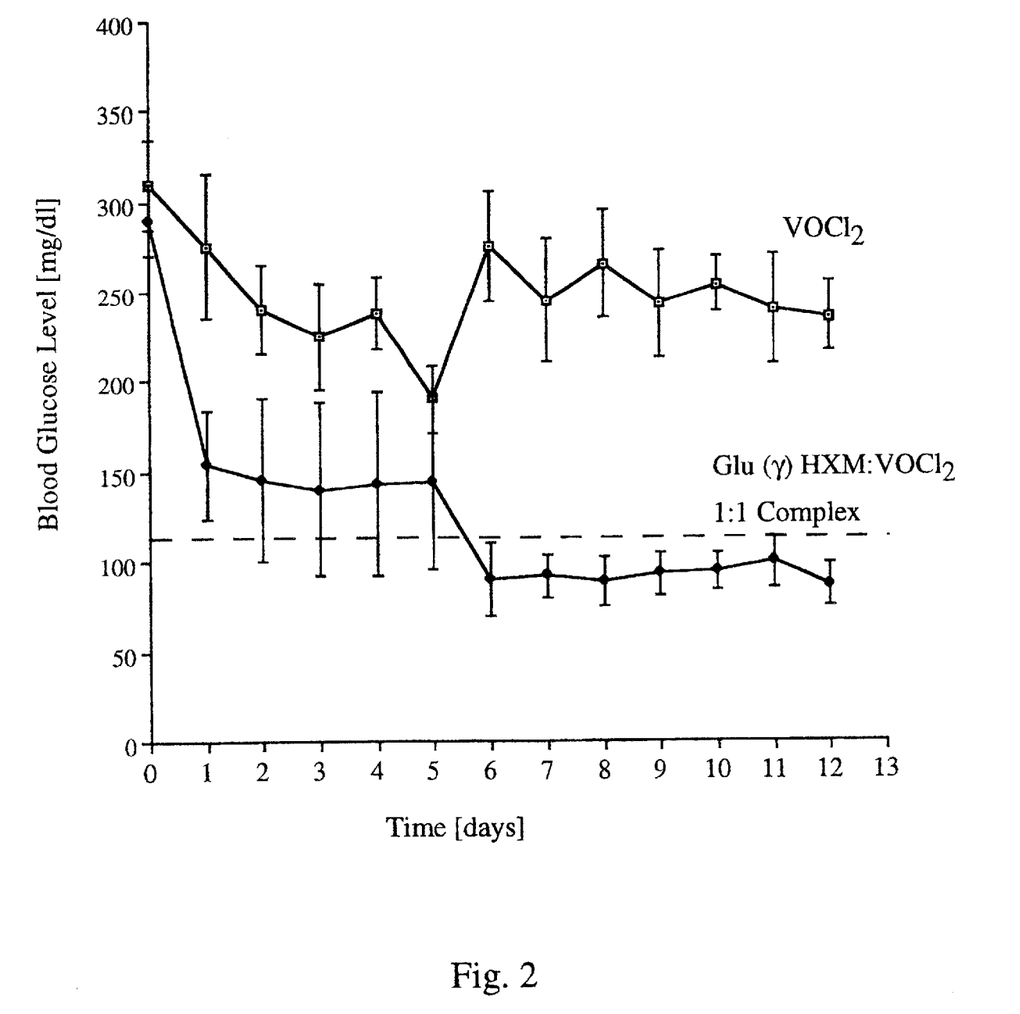
FIG. 2 shows that a 1:1 complex of Glu(γ)HXM:$VOCl_2$ (+4) potentiates the normoglycemic effect of vanadium in STZ-rats in comparison to free $VOCl_2$.

Effect of Glu(γ)HXM:VOCl$_2$ (1:1 Complex) on Blood Glucose Levels (BGL) of STZ-rats; Comparison to Low VOCl$_2$ Alone In order to show that vanadium (+4) amino acid monohydroxamate chelators potentiate the normoglycemia effect of vanadium in vivo, STZ-rats (see Experimental Procedures, section (b)), were given intraperitoneal (i.p.) injections of either VOCl$_2$ (0.02 mmol/kg/day) or of VOCl$_2$: Glu(γ)HXM 1:1 complex (0.02 mmol/kg rat/day). Blood glucose levels were measured over a period of 12 days. The results are depicted in FIG. 2, showing that daily i.p. injections of a low dosage of VOCl$_2$ by itself (approximately 2 mg vanadium/kg/day) had no significant effect on decreasing blood glucose levels, while the 1:1 complex of Glu(γ) HXM:VOCI2 (approximately 1 mg vanadium/kg/day) was effective and produced a dramatic decrease in blood glucose levels of STZ-rats toward normal values. Stable normoglycemia has been achieved within 2 days after administrating the complex, and persisted for several days following administration (FIG. 2, dashed line represents blood glucose levels of control healthy rats).

The amount of free vanadium (+4) required to induce normoglycemia, is 9.3 mg/kg/day (i.p. administration). Glu (γ)HXM:VOCl$_2$ complex (1:1) reduced the daily dosage to about 1 mg/kg/day (i.p. administration). Thus, in this in vivo STZ-rat model, complexation of vanadium (+4) to Glu(γ) HXM appears to potentiate vanadium (+4) about 9-fold.

Example 4

Figure 3:
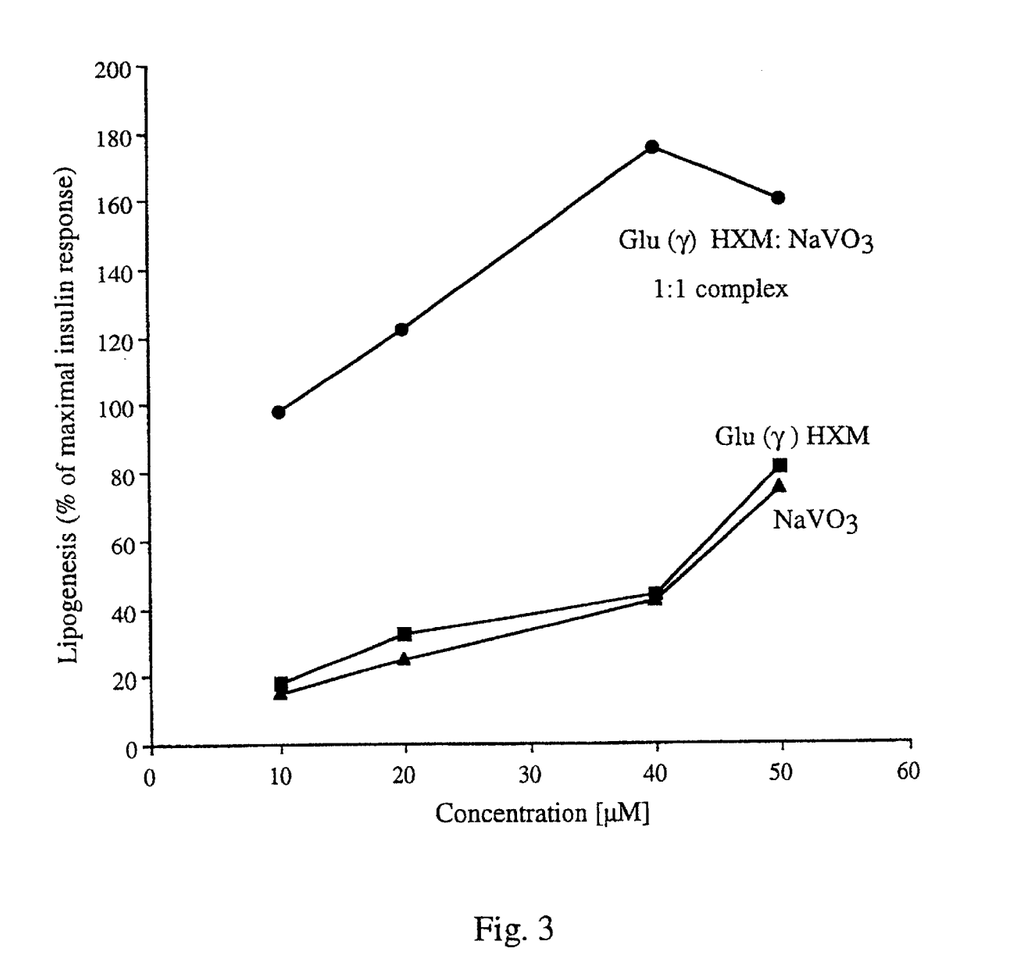
FIG. 3 shows concentration-dependent activation of lipogenesis by Glu(γ)HXM: $NaVO_3$ (1:1 complex), free $NaVO_3$ and free Glu(γ)HXM.

Monohydroxamates also Synergize the Insulinomimetic Potency of Vanadium (+5): L-Glu (γ)HXM Highly Potentiates the Vanadium (+5) to Activate Glucose Metabolism in Rat Adipocytes In order to test the synergistic effect of Glu(γ)HXM upon complexation with vanadate (+5), lipogenesis was performed as described in Experimental Procedures, section (c), with concentrations ranging from 10 μM to 50 μM of 1:1 complex of Glu(γ)HXM:VO$_4^{+3}$(+5), free Na$_3$VO$_4$ and free Glu(γ)HXM, respectively. Unlike with the dihydroxamate chelator designated RL-252 described in U.S. Pat. No. 5,338,759, that was found to potentiate the insulinomimetic capacity of vanadium (+4) but had no effect on, and even reduced, the potency of vanadium (+5) in vitro, Glu(γ)HXM dramatically potentiated the insulin-like effect of vanadate (+5) (FIG. 3). It is estimated that Glu(γ)HXM: VO$_4^{3+}$(+5) is at least 7-fold more potent in activating lipogenesis as compared to either free Na$_3$VO$_4$ or free Glu(γ)HXM.

Example 5

Glu(γ)HXM and Glu(γ)HXM:NaVO$_3$ (2:1) Complex Stimulate Hexose Influx

In order to test the specific effect of free Glu(γ)HXM and the Glu(γ)HXM:NaVO$_3$ (2:1) complex on the entrance of glucose into cells, an in vitro assay was performed using 2-deoxy-D-[6-$^3$H]glucose (2-DG). 2-DG is a non-metabolized analog of glucose and this assay thus represents the influence of a compound on glucose influx to cells, independent of glucose metabolism.

Freshly prepared adipocytes (3×10$^5$ cells/ml) suspended in KRB buffer pH 7.4, containing 1.0% BSA, were preincubated for 30 min, in the absence and the presence of insulin (17 nM), and the indicated concentrations (20 and 40 μM) of Glu(γ)HXM, Glu(γ)HXM:NaVO$_3$ (2:1) complex and NaVO$_3$. Aliquots (70 μl) of the aforementioned samples were transferred into tubes that contained 2-deoxy-D-[6-$^3$H] glucose (0.1 mM final concentration). After 3 minutes, phloretin (0.1 nM) was added in order to terminate the penetration of 2-DG into the cells. Samples of the suspended cells were then transferred to tubes with silicone oil where, upon centrifugation, the cells separate from the KRB medium and leftover 2-DG.

Figure 4:
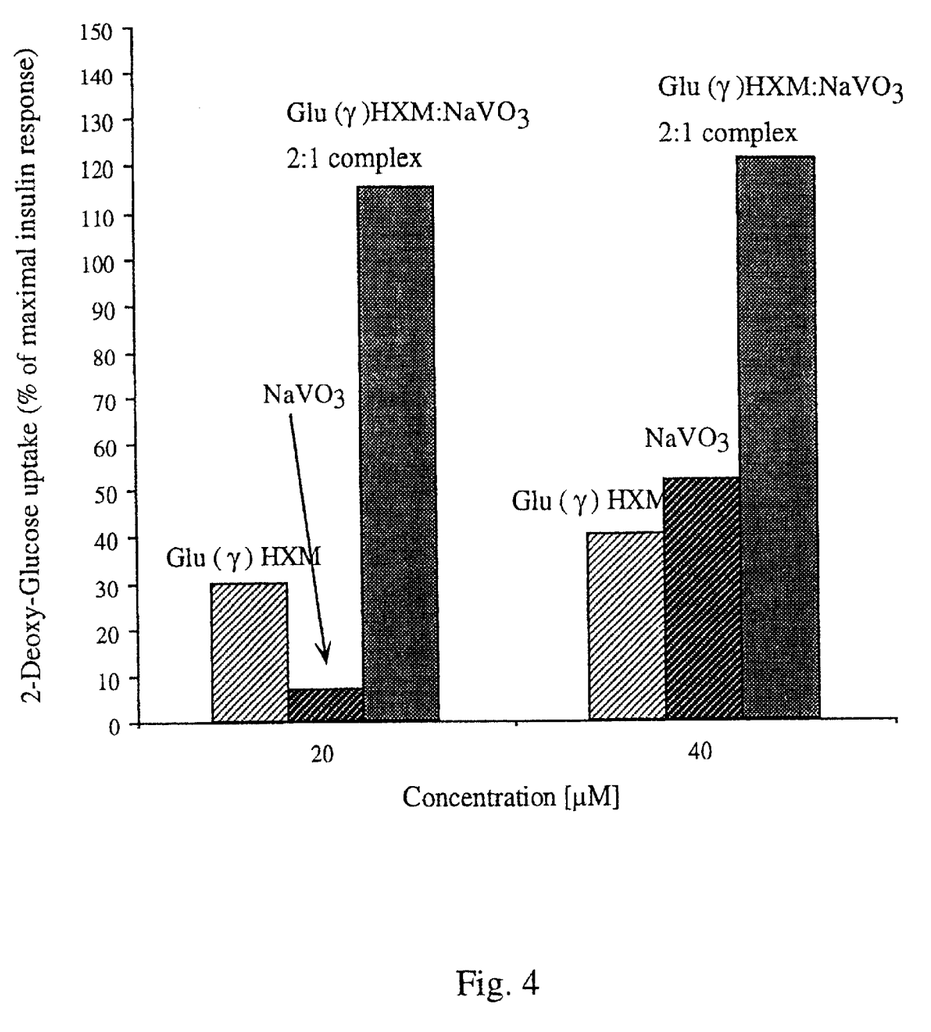
FIG. 4 shows that free Glu(γ)HXM, free $NaVO_3$ and a 2:1 complex of Glu(γ)HXM: $NaVO_3$ stimulate hexose influx at two different concentrations.

As shown in FIG. 4, free Glu(γ)HXM and Glu(γ)HXM:NaVO$_3$ (2:1) complex was found to activate glucose entry into the cells independently of glucose metabolism. The magnitude of the effect amounted to about 60% and 120%, respectively, of maximal insulin response.

Example 6

Figure 5:
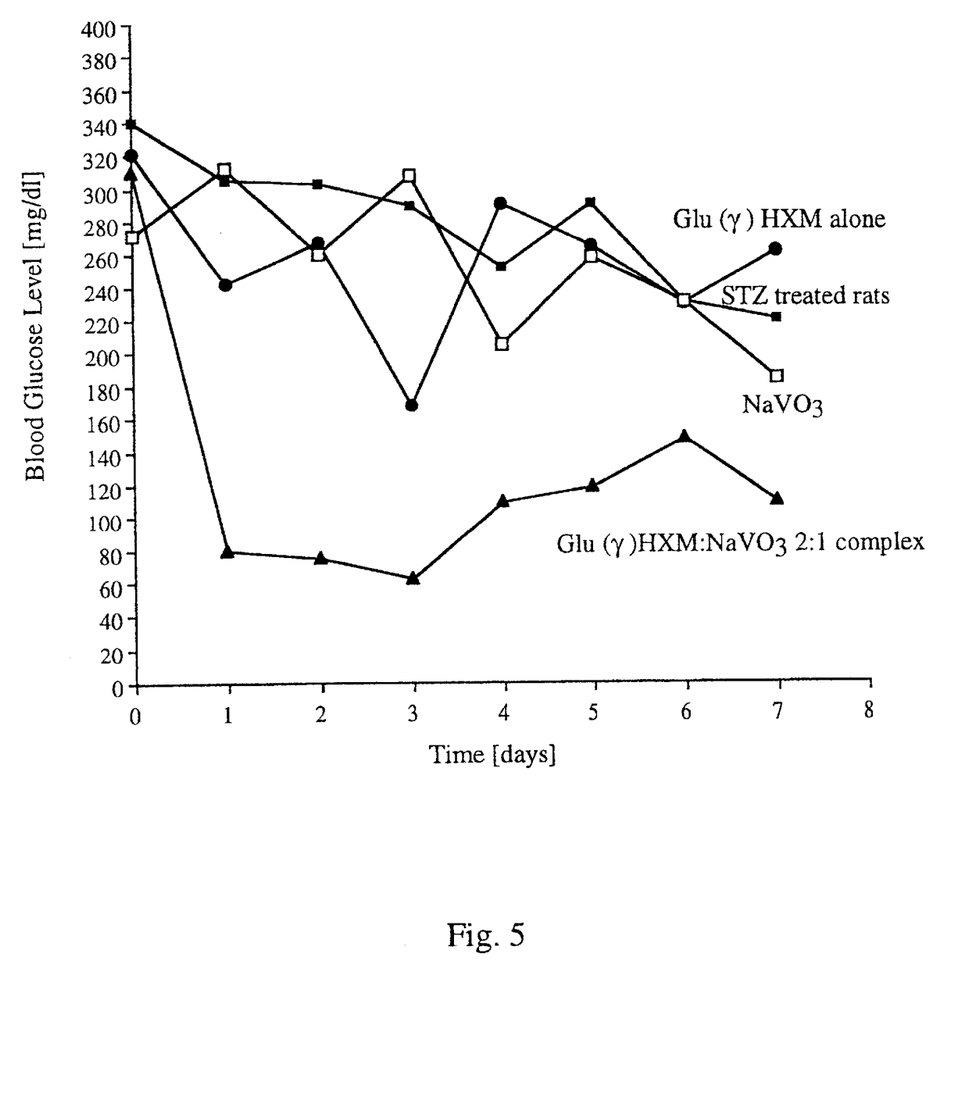
FIG. 5 shows that Glu(γ)HXM: $NaVO_3$ (2:1 complex) lowers blood glucose levels in STZ-treated rats in comparison to free Glu(γ)HXM and free $NaVO_3$.

Glu(γ)HXM:NaVO$_3$ (2:1) Complex Lowers Blood Glucose Levels in STZ-treated Rats In order to show that complexes of vanadium (+5) and monohydroxamate chelators potentiate the normoglycemic effect of vanadium in vivo and to test the normoglycemic effect of free Glu(γ)HXM in vivo, STZ-diabetic rats were divided into 4 groups of 4–5 rats each: diabetic control rats; vanadate (+5)-treated rats; Glu(γ)HXM:NaVO$_3$ (2:1) complex-treated rats ; and free Glu(γ)HXM-treated rats. Each group received daily i.p. injections of 0.05 mmol/kg (at 11.00 a.m.), of the corresponding compound. As shown in FIG. 5, after the first day (blood glucose level was measured at 8.00 a.m.) the blood glucose level of the complex-treated group reduced to normal levels.

Example 7

Figure 6:
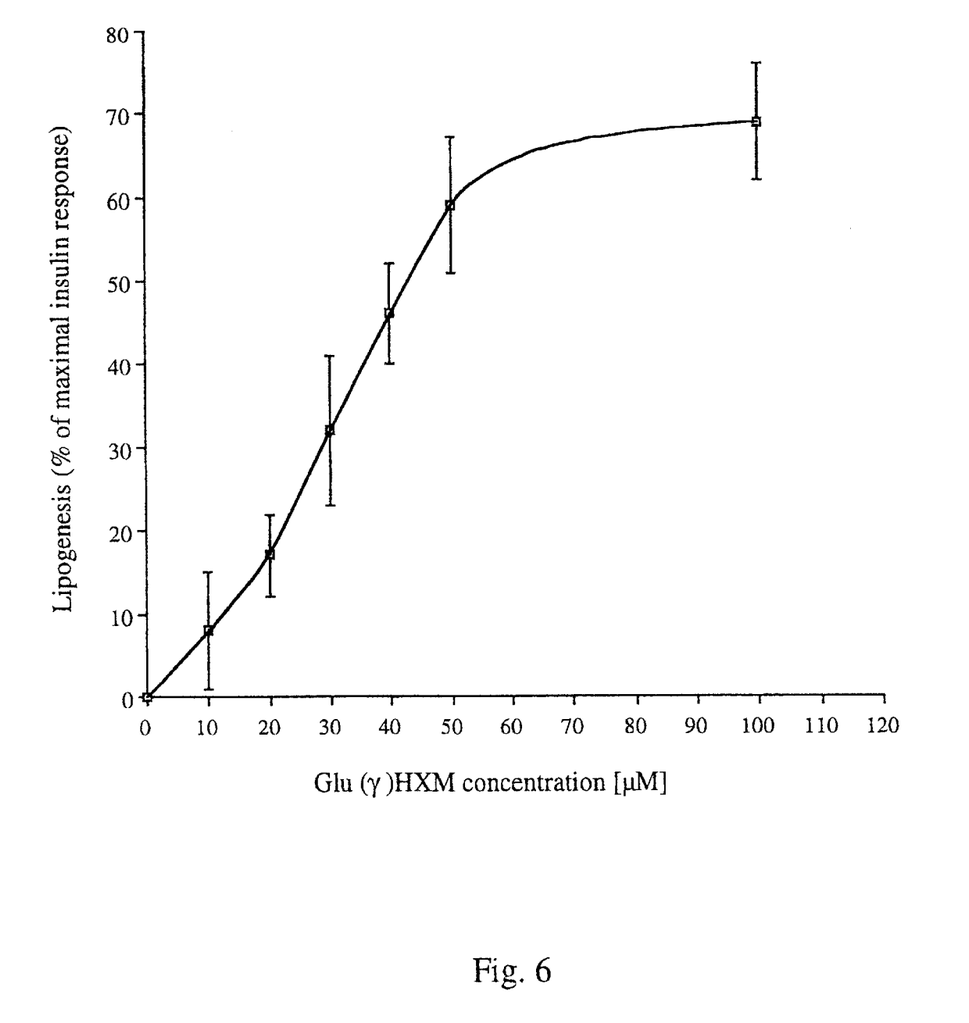
FIG. 6 shows that free Glu(γ)HXM activates lipogenesis in rat adipocytes in the absence of exogeneously added vanadium.

Glu(γ)HXM Activates Lipogenesis in Rat Adipocytes in the Absence of Exogeneously Added Vanadium In order to investigate the normoglycemic potential of free Glu(γ)HXM, lipogenesis was carried out as described above, using concentrations ranging between 10–100 μM of Glu(γ)HXM. As shown in FIG. 6, Glu(γ)HXM is, among all vanadium binders tested herein, unique in the capacity to produce insulin effects in the absence of exogeneously added vanadium. It is assumed that L-Glu(γ)HXM differs from all other amino acid-HXM in being capable of converting the minute quantity of intracellularly-located vanadium (~20 nM) into an insulinomimetically-active species.

Example 8

Staurosporine Inhibits Glu(γ)HXM-evoked Lipogenesis in Rat Adipocytes

Comparison to Staurosporine Effect on Insulin- and Vanadate-evoked Lipogenesis

Figure 7:
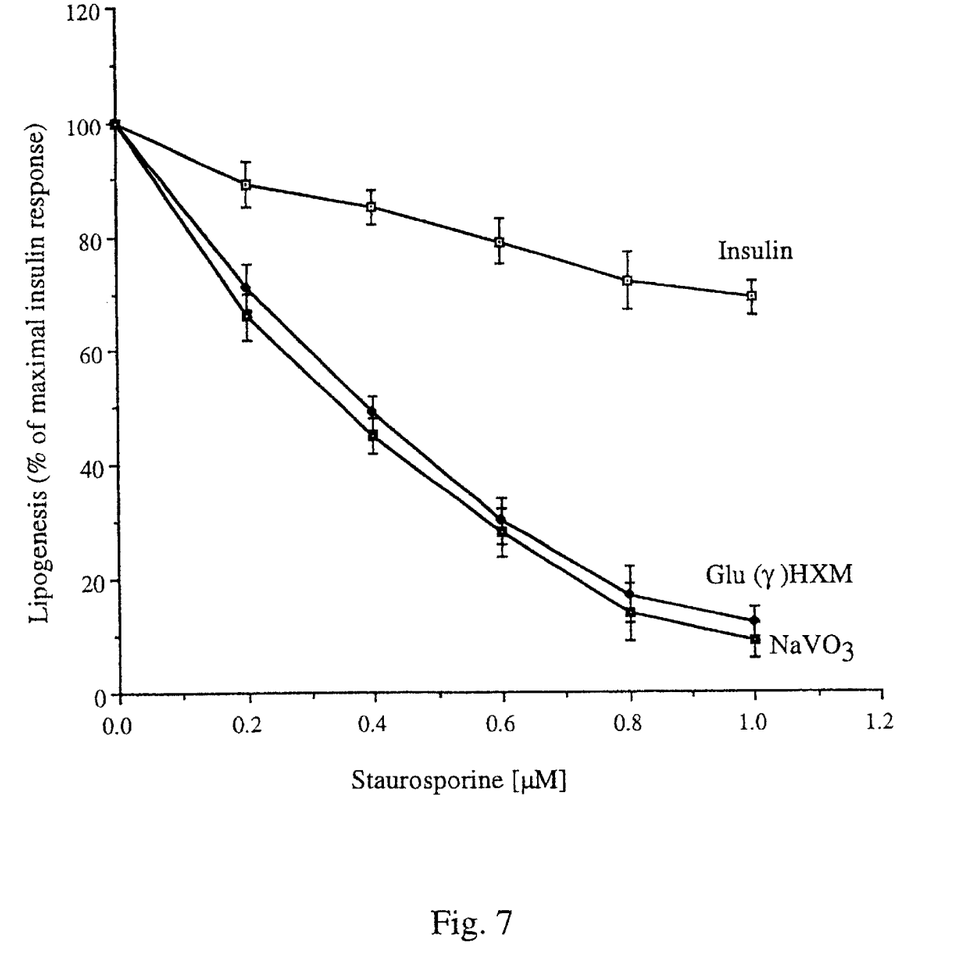
FIG. 7 shows the extent of lipogenesis evoked by either free Glu(γ)HXM, free NaVO$_3$ or insulin at increasing concentrations of staurosporine.

Staurosporine, a potent inhibitor of rat-adipose CytPTK (ki~2 nM) and a weak inhibitor of InsRTK (ki ~1 μM), preferentially inhibits the effect of vanadate in stimulating lipogenesis. In order to determine whether free Glu(γ)HXM also works through the vanadium pathway, adipocytes were subjected to various concentrations of staurosporine (as indicated in FIG. 7) for 30 min at 37° C. Lipogenesis was then carried out using adipocytes prepared as described above, in the presence of insulin (17 nM), sodium metavanadate (0.8 mM) or Glu(γ)HXM (100 μM). Maximal activation (100%) is that obtained with insulin, vanadate or Glu(γ)HXM in the absence of staurosporine.

FIG. 7 shows the extent of lipogenesis evoked by free Glu(γ)HXM, sodium metavanadate, or insulin at increasing concentrations of staurosporine. Activation of lipogenesis by Glu(γ)HXM was inhibited by staurosporine in a dose-dependent manner. The inhibition curve resembled that obtained for vanadate- (rather than that for insulin-) evoked lipogenesis, indicating that free Glu(γ)HXM works through vanadium (insulin-independent) pathway.

Example 9

Lipogenesis: Comparison Between Normal Adipocytes and Vanadiun-enriched Adipocytes, Treated with Glu(γ)HXM Free Glu(γ)HXM is unique in the sense of activating lipogenesis in rat adipocytes in the absence of exogeneously added vanadium. It is herein established that this effect is manifest through the vanadium pathway by experimental data showing that free Glu(γ)HXM is capable of converting the minute physiological quantity of endogeneously present vanadium in rat adipocytes into an insulinomimetically active species.

Figure 8:
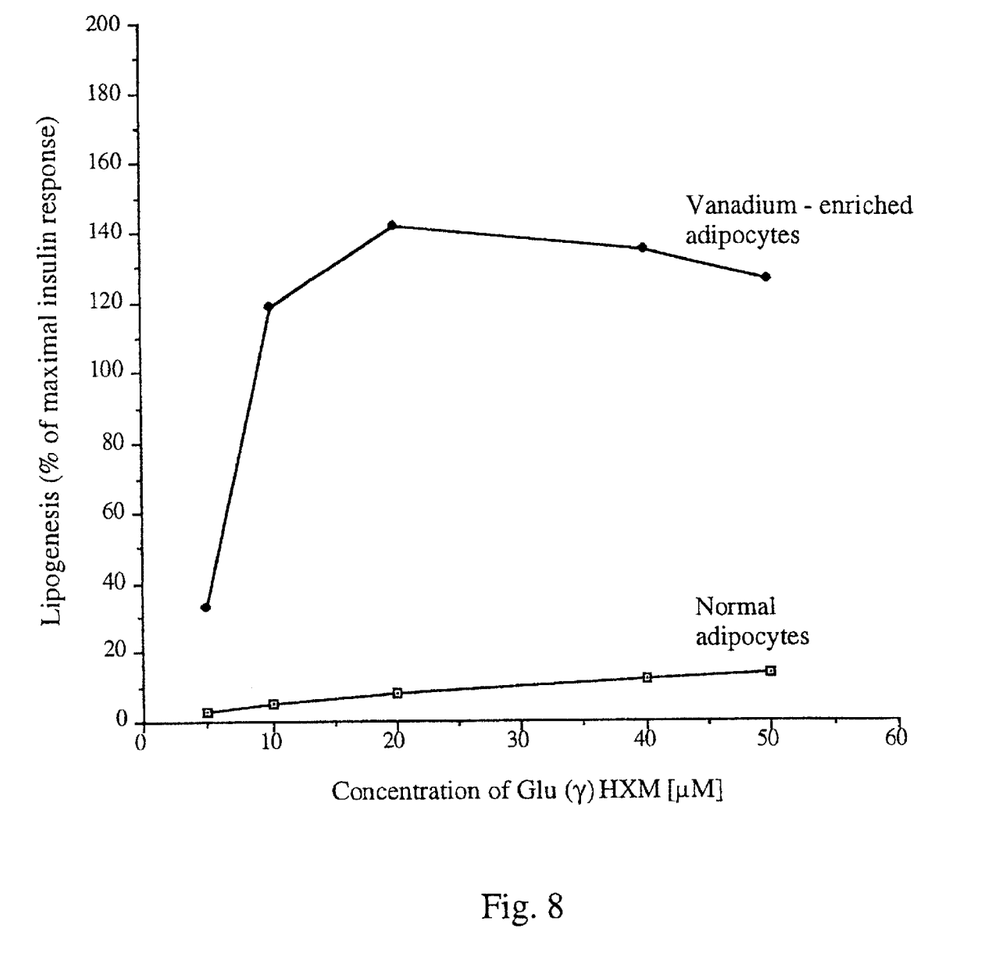
FIG. 8 shows a comparison of lipogenesis activation evoked by increasing concentrations of free Glu(γ)HXM in normal adipocytes and vanadium-enriched adipocytes.

To demonstrate this effect, male Wistar rats received daily subcutaneous (s.c.) injections of NaVO$_3$ (12 mg/kg/day)for five days (hereinafter designated "enriched-vanadium rats"). Lipogenesis was performed as described above using free Glu(γ)HXM to compare freshly prepared rat adipocytes ($3\times10^5$ cells/ml) from non-enriched vanadium rats to the enriched-vanadium rats. As shown in FIG. 8, the free Glu(γ)HXM was found to potentiate the effect of the intracellular vanadium in the enriched-vanadium rat cells to a much greater extent.

Example 10

Vanadium Complexes of Glu(γ)HXM are Stable

Figure 9:
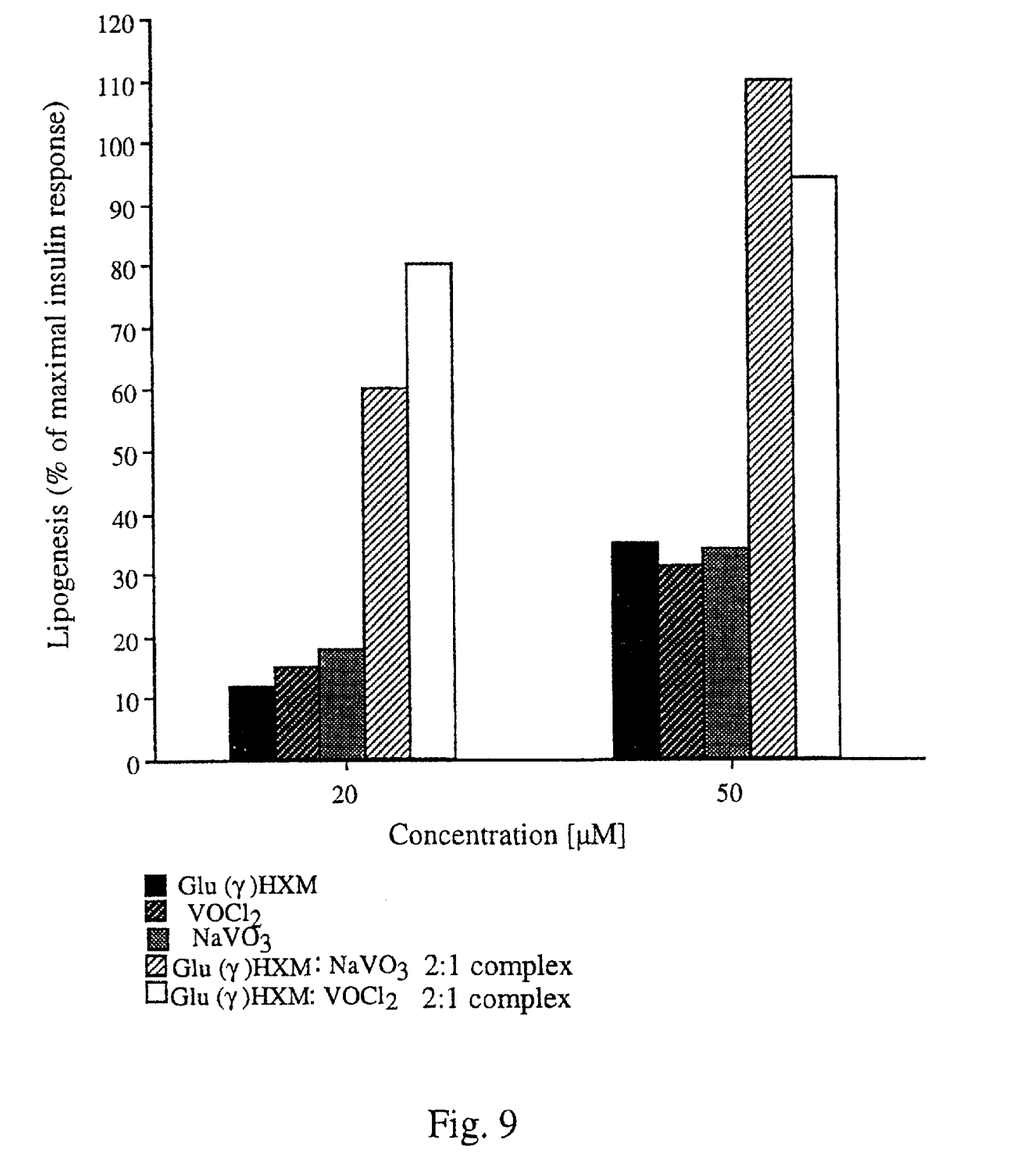
FIG. 9 shows a comparison of lipogenesis capacity of free Glu(γ)HXM, VOCl$_2$ and NaVO$_3$, and dry powder of Glu(γ) HXM:VOCl$_2$ and Glu(γ)HXM: NaVO$_3$ 2:1 complexes stored at room temperature.

To show that Glu(γ)HXM forms stable complexes with NaVO$_3$ and VOCl$_2$ that remain highly active during an extended period of time when kept as dry powder at room temperature, 2:1 complexes of Glu(γ)HXM: NaVO$_3$ and Glu(γ)HXM: VOCl$_2$ were prepared by dissolving the monohydroxamate and the vanadium salt in 2:1 equimolar concentrations, respectively, in water. The water solutions were then mixed, frozen with liquid nitrogen, and lyophilized. The dry powder obtained was allowed to stand at room temperature for 4 weeks. Lipogenesis was then performed as described above, using free Glu(γ)HXM, NaVO$_3$ and VOCl$_2$, and the Glu(γ)HNM: NaVO$_3$ and Glu(γ)HXM: VOCl$_2$2:1 complexes as dry powders. As shown in FIG. 9, both complexes maintained their level of insulinomimetic activity, indicating that they are stable.

REFERENCES

Brichard, S. M., and Henquin, J. C. (1995) Trends in Pharmacol. Sci. 16, 265–270.

Brown, D. A., R. A. Coogan, N. J. Fitzpatrick, W. K. Glass, D. E. Abukshima, L. Shiels, M. Ahlgren, K. Smolander, T. t. Pakkanen, T. A. Pakkanen and M. Perakyla (1996) J.Chem.Soc., Perkin Trans. 2, 2673–2679.

Cohen, N., Halberstam, M., Shimovich, P., Chang, C. R., Shamoon, H., and Rossetti, L. (1995) J. Clin. Invest. 95, 2051–2509.

Li, J., Elberg, G., Crans, D. C., and Shechter, Y. (1996) Biochemistry 35, 8314–8318.

Moody, A, Sta, M. A., Stan, M., and Gliemann, J. (1974) Horm. Metab. Res. 6, 12–16.

Rodbell, M (1964) J. Biol. Chem. 239, 375–80.

Sakurai et.al. (1995) BBRC,214,1095–1101.

Shechter, Y., Shisheva, A., Lazar, R., Libman, J. and Shanzer, A. (1992) Biochemistry 31, 2063–68.

Shechter, Y., Li, J., Meyerovitch, J., Gefel, D., Bruck, R., Elberg, G., Miller, D. S., and Shisheva, A., (1995) Molec. Cell. Biochem. 153, 39–47.

Tournaire, R., S. Malley, F. Hamedi-Sangsari, N. Thomasset, J. Grange, J. F. Dore and J. Vila,(1994) Int.J. Cancer 58, 420425.

Vila, J., N. Thomasset, C. Navarro and J. F. Dore (1990) Int.J.Cancer 45, 737–743.

What is claimed is:

1. A monohydroxamate vanadium complex of the formula (I):

R—CO—NHOH.X    (I)

wherein
R is a residue selected from the group consisting of:
(i) $H_2N$—CH(COY)—$(CH_2)_n$—
wherein n is 1,2 or 3, and Y is OH or $NH_2$;
(ii) $H_2N$—CH(COOH)—$CH_2$—S—$CH_2$—; and
X is a vanadium compound selected from the group consisting of a vanadyl ($VO^{2+}$), a metavanadate ($VO_3^-$) and a vanadate ($VO_4^{3-}$) salt.

2. The 1:1 or 2:1 vanadyl complex of L-glutamic acid γ-monohydroxamate according to claim 1, said complex having the formula:

$H_2N$—CH(COOH)—$CH_2$—$CH_2$—CO—NHOH: $VOCl_2$.

3. The 1:1 or 2:1 vanadate complex of L-glutamic acid γ-monohydroxamate according to claim 1, said complex having the formula:

$H_2N$—CH(COOH)—$CH_2$—$CH_2$—CO—NHOH: Na $VO_3$.

4. The vanadyl complex of L-aspartic acid, β-monohydroxamate according to claim 1, said complex having the formula:

$H_2N$—CH(COOH)—$CH_2$—CO—NHOH: $VOCl_2$.

5. A pharmaceutical composition comprising as active ingredient an effective amount of a vanadium complex of a monohydroxamate of the formula I:

R—CO—NHOH.X    (I)

wherein
R is a residue selected from the group consisting of:
(i) $H_2N$—CH(COY)—$(CH_2)_n$—
wherein n is 1,2 or 3, and Y is OH or $NH_2$;
(ii) $H_2N$—CH(COOH)—$CH_2$—S—$CH_2$—; and
X is a vanadium compound selected from the group consisting of a vanadyl ($VO^{2+}$), a metavanadate ($VO_3^-$) and a vanadate ($VO_4^{3-}$) salt.

6. The pharmaceutical composition according to claim 5, which is useful for the reduction of blood glucose levels and/or induction of normoglycemia in diabetic patients.

7. The pharmaceutical composition according to claim 6, in a form suitable for oral administration.

8. The pharmaceutical composition according to claim 5, wherein said active ingredient is selected from the group of vanadium complexes consisting of:

$H_2N$—CH (COOH)—$CH_2$—$CH_2$—CO—NHOH: $VOCl_2$
$H_2N$—CH (COOH)—$CH_2$—$CH_2$—CO—NHOH: Na $VO_3$ and
$H_2N$—CH (COOH)—$CH_2$—CO—NHOH: $VOCl_2$.

9. A pharmaceutical composition for the treatment of diabetes comprising;
(a) a vanadium compound selected from the group consisting of a vanadyl, a metavanadate and a vanadate salt, and
(b) a monohydroxamate of the formula R—CO—NHOH, wherein R is a residue selected from the group consisting of:
(i) $H_2N$—CH (COY)—$(CH_2)_n$—, wherein n is 1,2 or 3, and Y is OH or $NH_2$; and
(ii) $H_2N$—CH (COOH)—$CH_2$—S—$CH_2$—;

wherein said vanadium salt and said monohydroxamate are separated from one another in the composition.

10. A pharmaceutical package having two compartments:
(a) a first compartment containing a vanadium compound selected from the group consisting of a vanadyl, a metavanadate and a vanadate salt, and
(b) a second compartment containing a monohydroxamate of the formula R—CO—NHOH, wherein R is a residue selected from the group consisting of:
(i) $H_2N$—CH (COY)—$(CH_2)_n$—, wherein n is 1,2 or 3, and Y is OH or $NH_2$; and
(ii) $H_2N$—CH (COOH)—$CH_2$—S—$CH_2$—;

and instructions how to administer said vanadium salt and said monohydroxamate for reduction of blood glucose levels and/or induction of normoglycemia in diabetic patients.

11. A method for reducing blood glucose levels and/or inducing normoglycemia in a diabetic patient which comprises administering to said patient an effective amount of a vanadium complex of a monohydroxamate of the formula (I):

R—CO—NHOH.X    (I)

wherein
R is a residue selected from:
(i) $H_2N$—CH(COY)—$(CH_2)_n$
wherein n is 1,2 or 3, and Y is OH or $NH_2$; and
(ii) $H_2N$—CH (COOH)—$CH_2$—S—$CH_2$—;
X is a vanadium compound selected from the group consisting of a vanadyl ($VO^{2+}$), a metavanadate ($VO_3^-$) and a vanadate ($VO_4^{3-}$) salt.

12. The method according to claim 11, wherein said vanadium complex is the 1:1 or 2:1 vanadyl complex of L-glutamic acid γ-monohydroxamate of the formula:

$H_2N$—CH(COOH)—$CH_2$—$CH_2$—CO—NHOH: $VOCl_2$.

13. The method according to claim 11, wherein said vanadium complex is the 1:1 or 2:1 vanadate complex of L-glutamic acid γ-monohydroxamate, of the formula:

$H_2N$—CH(COOH)—$CH_2$—$CH_2$—CO—NHOH:Na $VO_3$.

14. The method according to claim 11, wherein said vanadium complex is the vanadyl complex of β-aspartic acid monohydroxamate of the formula:

$H_2N$—CH(COOH)—$CH_2$—CO—NHOH $VOCl_2$.

15. A method for inducing normoglycemia and/or reducing blood glucose levels in a diabetic patient which comprises administering to said patient an effective amount of a vanadium compound selected from the group consisting of a vanadyl, a metavanadate and a vanadate salt, and an effective amount of a monohydroxamate of the formula R—CO—NHOH, wherein R is a residue selected from the group consisting of:
(i) $H_2N$—CH(COY)—$(CH_2)_n$—,
wherein n is 1,2 or 3, and Y is OH or $NH_2$; and
(ii) $H_2N$—CH(COOH) —$CH_2$—S—$CH_2$—.

16. The method according to claim 15, wherein the vanadium compound is administered prior to the monohydroxamate compound.

17. The method according to claim 11, wherein said vanadium complex is administered orally.

18. The method according to claim 11, wherein the treatment is combined with administration of insulin.

* * * * *

UNITED STATES PATENT AND TRADEMARK OFFICE
CERTIFICATE OF CORRECTION

PATENT NO.     : 6,414,029 B1
DATED          : July 2, 2002
INVENTOR(S)    : Yoram Schechter et al.

It is certified that error appears in the above-identified patent and that said Letters Patent is hereby corrected as shown below:

<u>Title page,</u>
Item [75], delete "Goldwasher" and insert therefor -- Goldwaser --.

Signed and Sealed this

Fourth Day of January, 2003

JAMES E. ROGAN
*Director of the United States Patent and Trademark Office*